(12) United States Patent
Flohr et al.

(10) Patent No.: US 8,897,530 B2
(45) Date of Patent: Nov. 25, 2014

(54) METHOD, IMAGE PROCESSING DEVICE AND COMPUTED TOMOGRAPHY SYSTEM FOR DETERMINING A PROPORTION OF NECROTIC TISSUE AS WELL AS COMPUTER PROGRAM PRODUCT WITH PROGRAM SECTIONS FOR DETERMINING A PROPORTION OF NECROTIC TISSUE

(75) Inventors: Thomas Flohr, Uehlfeld (DE); Bernhard Schmidt, Fürth (DE); Martin Sedlmair, Forchheim (DE); Marcus Wagner, Obermichelbach (DE)

(73) Assignee: Siemens Aktiengesellschaft, Munich (DE)

( * ) Notice: Subject to any disclaimer, the term of this patent is extended or adjusted under 35 U.S.C. 154(b) by 359 days.

(21) Appl. No.: 13/433,989

(22) Filed: Mar. 29, 2012

(65) Prior Publication Data

US 2012/0250967 A1 Oct. 4, 2012

(30) Foreign Application Priority Data

Mar. 30, 2011 (DE) .......................... 10 2011 006 398

(51) Int. Cl.
*G06T 7/00* (2006.01)
*A61B 6/12* (2006.01)
*A61B 6/00* (2006.01)
*G06T 7/60* (2006.01)

(52) U.S. Cl.
CPC ............... *A61B 6/481* (2013.01); *G06T 7/0081* (2013.01); *G06T 2207/10152* (2013.01); *G06T 2207/30096* (2013.01); *A61B 6/482* (2013.01); *A61B 6/12* (2013.01); *G06T 2207/10116* (2013.01); *A61B 6/5217* (2013.01); *G06T 2207/20148* (2013.01); *G06T 7/602* (2013.01); *G06T 7/0097* (2013.01)
USPC .......................................... 382/131; 382/132

(58) Field of Classification Search
None
See application file for complete search history.

(56) References Cited

U.S. PATENT DOCUMENTS 4,922,915 A * 5/1990 Arnold et al. ................. 382/128
2005/0281381 A1 12/2005 Guendel
(Continued)

FOREIGN PATENT DOCUMENTS

DE 102004027710 A1 1/2006
DE 102006009222 B4 2/2008

OTHER PUBLICATIONS

Veredas et al. "Binary Tissue Classification on Wound Images with Neural Networks and Bayesian Classifiers." IEEE Transactions on Medical Imaging, vol. 29, No. 2, Feb. 2010, pp. 410-427.*

(Continued)

*Primary Examiner* — Jon Chang
(74) *Attorney, Agent, or Firm* — Harness, Dickey & Pierce, P.L.C.

(57) ABSTRACT

An image processing device and method are disclosed for determining a proportion of necrotic tissue in a defined tissue area of an object under examination based on a high-energy image dataset and a low-energy image dataset, each recorded by way of x-ray measurements with different x-ray energies after a contrast medium has been applied to the object under examination. In at least one embodiment of the method, a virtual contrast medium image is determined from the high-energy image dataset and the low-energy image dataset and a segmentation image dataset is created, by the area of tissue being segmented. The segmentation result is transferred into the virtual contrast medium image for segmenting the tissue area in the virtual contrast medium image. Finally an analysis of values of the pixels lying in the segmented area is undertaken for identifying pixels which are to be assigned to necrotic tissue.

22 Claims, 4 Drawing Sheets

(56) References Cited

U.S. PATENT DOCUMENTS

2007/0217570 A1   9/2007  Grasruck et al.
2009/0086905 A1*  4/2009  Boyden et al. .................. 378/46
2010/0014737 A1*  1/2010  Ruhrnschopf et al. ........ 382/131

OTHER PUBLICATIONS

Constantin et al. "Unsupervised Segmentation of Brain Tissue in Multivariate MRI." IEEE International Symposium on Biomedical Imaging: From Nano to Macro, Apr. 2010, pp. 89-92.*

Mandava et al. "Osteosarcoma Segmentatino in MRI using Dynamic Harmony Search Based Clustering." International Conference of Soft Computing and Pattern Recognition, Dec. 2010, pp. 423-429.*

Gaonkar at al. "Automated Segmentation of Cortical Necrosis Using a Wavelet Based Abnormality Detection System." IEEE International Symposium on Biomedical Imaging: From Nano to Macro, Mar. 30, 2011, pp. 1391-1395.*

Caucci et al. "Adaptive SPECT for Tumor Necrosis Detection." IEEE Nuclear Science Symposium Conference Record, Oct. 2008, pp. 5548-5551.*

Otsu N. "A Threshold Selection Method From Gray-Level Histograms", IEEE Transactions on Systems, Man, and Cybernetics, vol. SMC-9, No. 1, Jan. 1979, pp. 62-66, Magazine.

Nobuyuki Otsu, A Threshold Selection Method From Gray-Level Histograms, In IEEE Transactions on Systems, Man, and Cybernetics, vol. SMC-9, No. 1, Jan. 1979, pp. 62-66; Magazine.

Dual Energy CT: Physikalische Modelle und Anwendungen, Martin Ulrich Sedlmair; Martin Ulrich Sedlmair, Dual Energy CT: Physikalische Modelle und Anwendungen, Dissertation an der Medizinischen Fakultät der Ludwig-Maximilians-Universität zu München; München 2009, Auszug: pp. 108-113.

Janet Cochrane Miller et al; "Multi-Energy Computed Tomography—New Opportunities in Imaging the Abdomen"; Radiology Rounds, vol. 8, No. 9, The abstract pp. 2 §§ 1-2, pp. 3 § 1; claims 1-14; 2010; US; Sep. 30, 2010.

Kang Li et al; "Simultaneous Detection of Multiple Elastic Surfaces with Application to Tumor Segmentation in CT Images"; Medical Imaging 2008: Image processing; vol. 6914; Section 1 $ 4, Fig. 4; Claims No. 1-14; 2008; US; Feb. 16, 2008.

Long-Jiang Zhang et al; "Liver virtual non-enhanced CT with dual-source, dual-energy CT: a preliminary study"; Eur Radiol, vol. 20; Full text; Claims 1-14; 2010; Apr. 15, 2010.

Chinese Office Action and English translation thereof dated Mar. 5, 2014, For Chinese patent application No. 2012100904242.

German Office Action mailed Oct. 29, 2012, for German patent application No. 10 2011 006 398.6.

* cited by examiner

METHOD, IMAGE PROCESSING DEVICE AND COMPUTED TOMOGRAPHY SYSTEM FOR DETERMINING A PROPORTION OF NECROTIC TISSUE AS WELL AS COMPUTER PROGRAM PRODUCT WITH PROGRAM SECTIONS FOR DETERMINING A PROPORTION OF NECROTIC TISSUE

PRIORITY STATEMENT

The present application hereby claims priority under 35 U.S.C. §119 to German patent application number DE 10 2011 006 398.6 filed Mar. 30, 2011, the entire contents of which are hereby incorporated herein by reference.

FIELD

At least one embodiment of the invention relates to a method, an image processing device and a computed tomography system for determining a proportion of necrotic tissue in a defined tissue area, especially of a tumor of an object under examination. The invention also relates to a computer program product with program code sections for determining a proportion of necrotic tissue in a defined tissue area, especially of a tumor, of an object under examination.

BACKGROUND

It is important in the therapy of tumor diseases to check the success of the therapy by regular progress examinations, in order to decide in good time whether a therapy is to be continued or not or whether a change of therapy would be more sensible. In the estimation of the therapy success, however, as well as establishing the size of the tumorous tissue, the determination of the proportion of necrotic tissue in the tumor volume is of importance, since tumors react differently to different forms of therapy and do not necessarily change their shape, but merely die off partly or completely, i.e. necrotize.

There is also the danger with biopsies of a suspected lesion that only tissue which is already dead, i.e. necrotic tissue, will be removed with the biopsy needle, which is not suitable for a further examination. Information about the geometric location of the vital or the necrotic proportion of a tumor is also valuable in carrying out the biopsies, in order to ensure that vital tissue is removed.

In a previously usual method to enable the necrotic proportion of tumor tissue to be determined, a contrast medium examination is introduced using a single-source computed tomograph. With such an examination two recordings or two scans are carried out. The first of the two recordings is a native recording made without contrast medium, while at least one second recording is made after introduction of the contrast medium, mostly iodine. The contrast medium temporarily accumulates in the tumor, wherein the necrotic tissue does not take up any contrast medium, since it is dead. Frequently a number of images are recorded after the addition of contrast medium, even a number of images in different accumulation phases in the tissue, for example in an arterial, a venous and in a late venous phase, in order in this way to obtain additional information about the vital tissue by its iodine take-up behavior.

To determine the necrotic tissue a differentiation could be carried out on the basis of image datasets obtained by these measurements. To do this the values of the respective pixels of the two image datasets are subtracted from one another. A pixel is to be understood below as a voxel or pixel depending on whether three-dimensional or two-dimensional image data is involved. Within the context of the invention the values of the pixel accordingly generally involve intensity values, such as Hounsfield values (unit HU), which are a measure of the attenuation of the x-rays arising at this pixel. However this subtraction method requires an exact alignment and adaptation of the recorded tissue sections or of the tumor tissue in the different image datasets to one another. Since a certain period of time elapses between the two recordings, there can be patient movements and/or deformations of the tumor tissue as a result of the often soft tissue structure in the intervening period. These tissue displacements can in fact mostly be compensated for in a non-rigid, i.e. elastic registration. However these types of methods require large computer capacities and unfortunately also do not always deliver straightforward results. Thus this method is hardly ever used in clinical practice.

SUMMARY

At least one embodiment of the invention provides a method, an image processing device, a computed tomography system and/or a computer program product which delivers improved results with a reduced data-processing effort.

At least one embodiment of the inventive method is for determining a proportion of necrotic tissue in a defined tissue area of an object under examination is performed on the basis of a high-energy image dataset comprising the tissue area of the object under examination and a low-energy image dataset comprising the tissue area of the object under examination. The high-energy image dataset comprising the tissue area of the object under examination and the low-energy image dataset comprising the tissue area of the object under examination are recorded beforehand by way of x-ray measurement with different x-ray energy after injection of a contrast medium to the object under examination or for example created by reconstruction methods known per se, especially back projections from the projection datasets obtained with these measurements.

An inventive image processing device of at least one embodiment, for determining a proportion of necrotic tissue in a defined tissue area of an object under examination accordingly comprises the following components:
- an image dataset interface for reading in a high-energy image dataset comprising the tissue area of the object under examination and a low-energy image dataset comprising the tissue area of the object under examination, which have been created by means of x-ray measurements with different x-ray energies after a contrast medium injection at the object under examination;
- a contrast medium image determination unit which is embodied to determine a virtual contrast medium image based on the high-energy image dataset and the low-energy image dataset;
- a segmentation unit which is embodied to segment the tissue area into a segmentation image dataset based on the high-energy image dataset and/or the low-energy image dataset;
- a referencing unit, which is embodied to transfer a segmentation result into the virtual contrast medium image for segmenting the tissue area in the virtual contrast medium image; and
- an analysis unit, which is embodied to carry out an analysis of values of pixels belonging to the area of the virtual contrast medium image to be segmented, to identify pixels which are to be assigned to necrotic tissue.

Such an image processing device can be a part of a computed tomography system, i.e. it can for example be installed on a control or evaluation processor of the computed tomography system. Accordingly a computed tomography system, preferably a dual-source tomography system, with such an image processing device also belongs to the image processing device. Basically such an image processing device can also be realized on a self-contained processor unit such as a pure evaluation unit of a radiological network or the like, which is connected for example to a computed tomography system for data transfer or can be supplied with corresponding data in another way.

At least one embodiment of the invention comprises a computer program product which is able to be loaded directly into a memory of such an image processing device, with program code sections to perform all steps of at least one embodiment of the inventive method. Such a software realization has the advantage that already existing image processing devices which are used for analysis of corresponding image data (for example suitable control devices of computed tomography systems), can be modified by implementing the program in a suitable manner in order to operate in accordance with at least one embodiment of the inventive method.

BRIEF DESCRIPTION OF THE DRAWINGS

The invention will be explained once more in greater detail below with reference to the enclosed figures on the basis of example embodiments. In the explanation identical components are provided with identical reference numbers in the figures, in which.

Figure 1:
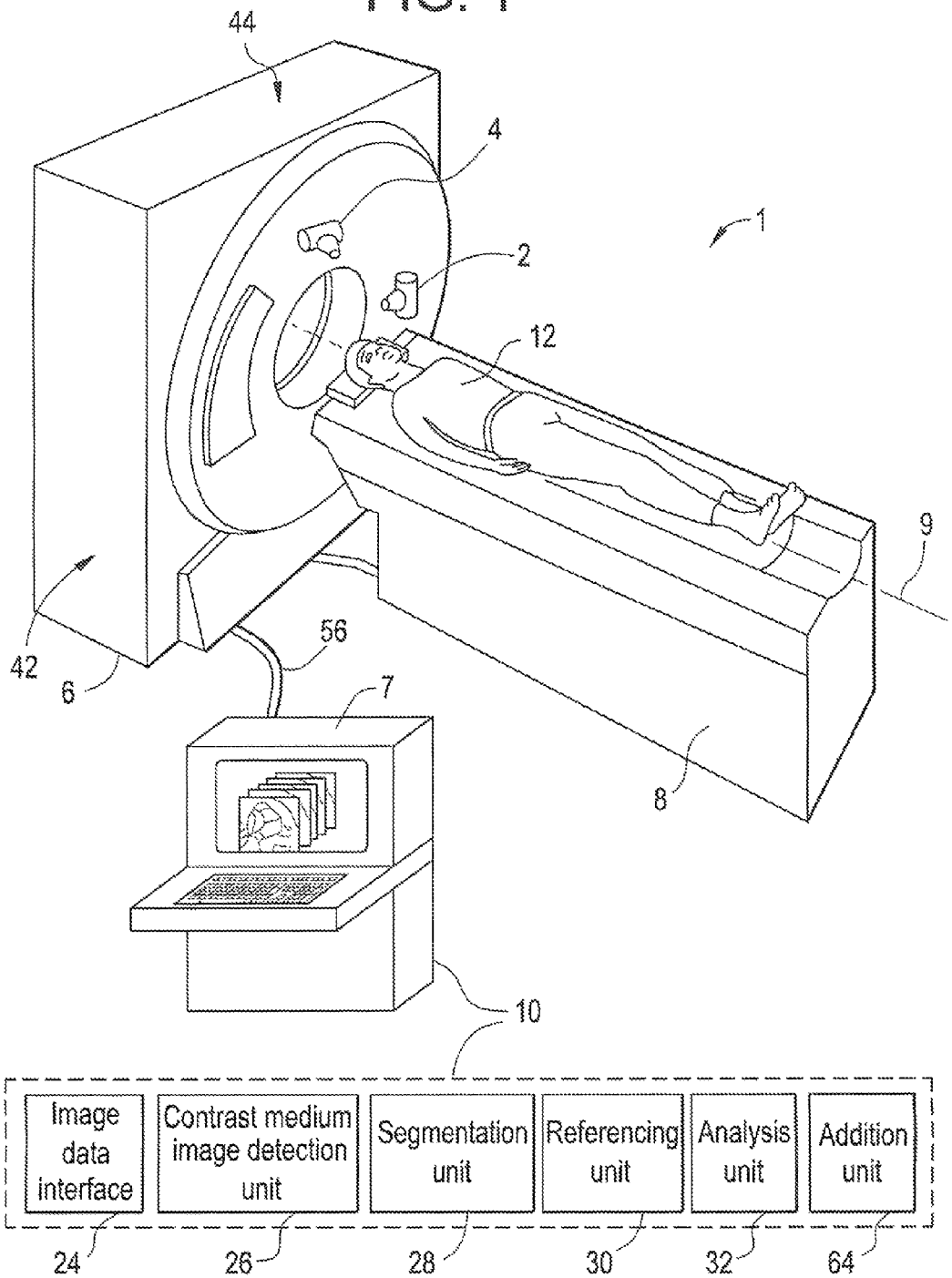
FIG. 1 shows a schematic diagram of an example embodiment of an inventive computed tomography system with an image processing device.

It should be noted that these Figures are intended to illustrate the general characteristics of methods, structure and/or materials utilized in certain example embodiments and to supplement the written description provided below. These drawings are not, however, to scale and may not precisely reflect the precise structural or performance characteristics of any given embodiment, and should not be interpreted as defining or limiting the range of values or properties encompassed by example embodiments. For example, the relative thicknesses and positioning of molecules, layers, regions and/or structural elements may be reduced or exaggerated for clarity. The use of similar or identical reference numbers in the various drawings is intended to indicate the presence of a similar or identical element or feature.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

At least one embodiment of the inventive method is for determining a proportion of necrotic tissue in a defined tissue area of an object under examination is performed on the basis of a high-energy image dataset comprising the tissue area of the object under examination and a low-energy image dataset comprising the tissue area of the object under examination. The high-energy image dataset comprising the tissue area of the object under examination and the low-energy image dataset comprising the tissue area of the object under examination are recorded beforehand by way of x-ray measurement with different x-ray energy after injection of a contrast medium to the object under examination or for example created by reconstruction methods known per se, especially back projections from the projection datasets obtained with these measurements.

In accordance with an embodiment of the invention a virtual contrast medium image is first obtained on the basis of the high-energy image dataset and low-energy image dataset obtained in the first step. The determination of a virtual contrast medium image as well as a virtual native image from high-energy image datasets and low-energy image datasets is known for example from DE 10 2006 009 222 B4, the entire contents of which are hereby incorporated herein by reference, and is thus familiar to the person skilled in the art. Such a virtual (pure) contrast medium image is a representation of only the tissue in the defined tissue area through which contrast medium passes and can thus for example, within the context of the present invention, represent the proportions of vital tissue in the defined tissue area.

In a further step, the defined tissue area is segmented into a segmentation image based on the high-energy image dataset and/or the low-energy image dataset. Through the segmentation the outer limits of the defined tissue area for example of the tumor, including the necrotic and vital tissue, are determined. The segmentation thus allows inter alia a determination of the overall volume of the defined tissue area.

In principle the segmentation image dataset can just simply include the high-energy image dataset or the low-energy image dataset, i.e. the segmentation of the defined tissue area can be undertaken directly in the high-energy image dataset or in the low-energy image dataset if the contrast in the high-energy or low-energy image dataset allows this. As will be explained later, it is often advantageous, on the basis of the high-energy and the low-energy image dataset, to create an extra segmentation image dataset which exhibits a better contrast than the high-energy image dataset for example and thus facilitates the segmentation of the tissue area.

In a subsequent step the segmentation result in the virtual contrast medium image is transferred for segmentation of the defined tissue area into the virtual contrast medium image. The segmentation result involves the information with which the defined tissue area is able to be precisely defined or determined in the image data, e.g. it involves location information over all pixels (i.e. voxels or pixels) belonging to the defined tissue area or information about the outer limits of the defined tissue area. Thus the contrast medium image, in addition to information about the sections of tissue through which the contrast medium passes, is also assigned information about the complete defined tissue area, i.e. the defined tissue area can also be uniquely completely identified within the virtual contrast medium image, which itself only shows the vital tissue and can be separated within the framework of the segmentation for example from the remaining image data in the virtual contrast medium image.

Finally values of pixels belonging to the segmented area of the virtual contrast medium image are analyzed to identify such pixels to which necrotic tissue is to be assigned. I.e. the intensity values of all voxels or pixels which lie within the segmented area in the virtual contrast medium image and thus can be assigned uniquely to the defined tissue area, e.g. the tumor, are evaluated as to whether the intensity value of the voxel or pixel is indexed to necrotic tissue or to vital tissue. Thus two groups of pixels are present as a result of the analysis in an area of the virtual contrast medium image to be assigned uniquely to the defined tissue area, which on the one hand can be assigned to the necrotic tissue and on the other to the vital tissue.

An advantage that at least one embodiment of the method has over the conventional method is that a native image is not needed as a reference image for a contrast medium image. Instead the image data is merely used from two contrast medium measurements with different x-ray energies. The measurements with the different x-ray energies can however be carried out almost simultaneously or at least very shortly after one another, unlike the recordings for a native image and a contrast medium image between which a waiting time is to be maintained, in which the contrast medium accumulates in the tissue to be examined. A complicated registration of the image datasets used with one another to avoid movement artifacts is consequently not necessary with at least one embodiment of the inventive method. This not only saves computing time but also makes the determination method less susceptible to errors and thus makes the result qualitatively better. In addition the overall dose to which a patient is subjected in such a measurement is generally lower with the method in accordance with at least one embodiment of the invention than it is with conventional methods.

As already stated above, at least one embodiment of the inventive method is especially valuable in an evaluation of the success of a therapy for tumor treatment. Accordingly the defined tissue area preferably comprises tumor tissue or is formed by a delimitable tumor. Embodiments of the invention is not however restricted to use in a tumor progress examination. In principle the defined tissue area can involve any given spatially and/or functionally-delimitable tissue object, especially also an organ such as e.g. heart liver or lungs. Likewise the defined tissue area can also involve a definable section or a functional part of an organ or the like, such as an entire specific heart muscle, a specific blood vessel etc. for example.

An inventive image processing device of at least one embodiment, for determining a proportion of necrotic tissue in a defined tissue area of an object under examination accordingly comprises the following components:

an image dataset interface for reading in a high-energy image dataset comprising the tissue area of the object under examination and a low-energy image dataset comprising the tissue area of the object under examination, which have been created by means of x-ray measurements with different x-ray energies after a contrast medium injection at the object under examination;

a contrast medium image determination unit which is embodied to determine a virtual contrast medium image based on the high-energy image dataset and the low-energy image dataset;

a segmentation unit which is embodied to segment the tissue area into a segmentation image dataset based on the high-energy image dataset and/or the low-energy image dataset. This segmentation unit can be embodied in the simplest case so that it carries out the segmentation as required in the high-energy image dataset or in the low-energy image dataset. The image processing device can however, for example as part of the segmentation unit, in a preferred embodiment, have a segmentation image dataset creation unit which allows a segmentation image dataset to be created based on the high-energy image dataset and/or the low-energy image dataset, so that the segmentation unit carries out the segmentation on said dataset.

a referencing unit, which is embodied to transfer a segmentation result into the virtual contrast medium image for segmenting the tissue area in the virtual contrast medium image and an analysis unit, which is embodied to carry out an analysis of values of pixels belonging to the area of the virtual contrast medium image to be segmented, to identify pixels which are to be assigned to necrotic tissue.

Such an image processing device can be a part of a computed tomography system, i.e. it can for example be installed on a control or evaluation processor of the computed tomography system. Accordingly a computed tomography system, preferably a dual-source tomography system, with such an image processing device also belongs to the image processing device. Basically such an image processing device can also be realized on a self-contained processor unit such as a pure evaluation unit of a radiological network or the like, which is connected for example to a computed tomography system for data transfer or can be supplied with corresponding data in another way.

In particular the contrast medium image determination unit, the segmentation unit, if necessary the segmentation image dataset generation unit, the referencing unit and the analysis unit can each be realized as software modules on a suitable computer with corresponding storage facilities. The image dataset interface can also be realized in the form of pure software, provided only an acceptance of the high-energy and low-energy image datasets from other program units is required. Basically the image dataset interface can however also be realized as a combined hardware/software interface in order to implement an external input.

At least one embodiment of the invention comprises a computer program product which is able to be loaded directly into a memory of such an image processing device, with program code sections to perform all steps of at least one embodiment of the inventive method. Such a software realization has the advantage that already existing image processing devices which are used for analysis of corresponding image data (for example suitable control devices of computed tomography systems), can be modified by implementing the program in a suitable manner in order to operate in accordance with at least one embodiment of the inventive method.

The dependent claims and the further description contain especially advantageous embodiments and developments of the invention, wherein especially the claims of one category can also be developed in accordance with the claims of another category.

In principle for carrying out the method in accordance with at least one embodiment of the invention, a low-energy image dataset and a high-energy image dataset can be transferred, which for example have already been measured previously on a device. Likewise an already-measured low-energy projection dataset and a high-energy projection dataset can also be transferred and within the context of the inventive method the image datasets will be reconstructed from said datasets. The data can in such cases be transferred via a network for example.

In one variant however, at least one embodiment of the inventive method itself comprises the recording of the high-energy image dataset comprising the tissue area of the object under examination and of the low-energy image dataset comprising the tissue area of the object under examination by way of x-ray measurement with different x-ray energies after the injection of contrast medium at the object under examination. I.e., in at least one embodiment, the complete method is started with the measurement and subsequently is undertaken directly on the basis of the measurement data, for example on a control device of the computed tomograph, for determination of the proportion of necrotic tissue in the defined examined tissue area. "X-ray energy" is generally specified with such measurements by a defined value, for example by the x-ray tube voltage (i.e. the extraction voltage for the electrons), even if an x-ray energy does not correspond to any discrete values, but naturally always comprises an energy spectrum with a certain bandwidth around the specified value. Typical x-ray energies for a computed tomography dual-energy measurement lie at around 80 kV for the low-energy image dataset and 140 kV for the high-energy image dataset.

The measurements with the different energies are sensibly made in such cases within a short time interval. In such cases a short time interval is understood as a period of time within which the contrast medium concentration in the object under examination changes by a maximum of 5%.

Any given computed tomography system can in principle be used to record the high-energy image dataset and the low-energy image dataset.

As mentioned above, at least one embodiment of the method can be used to particular advantage if the period of time between the measurement of the high-energy image dataset and of the low-energy image dataset is as short as possible, so that no significant movements of the object under examination or at least of the part of the object under examination to be recorded occur between the high-energy image dataset and the low-energy image dataset. This can be guaranteed for example if a computed tomography system has a detector width in the direction of advance which covers the entire defined tissue area, e.g. the tumor. With this type of computed tomography system the high-energy measurement and the low-energy measurement can then be carried out directly after one another during the orbit of the x-ray source around the longitudinal tomograph axis (which corresponds to the direction of advance) one after the other (in any given sequence). For recording a projection dataset sufficient for reconstruction of an image dataset of the defined tissue area, with such a detector width only one orbit of the x-ray source by at least 180° plus the beam angle of the x-ray sources is necessary. Then after recording the first projection dataset there can be a switchover from a first x-ray voltage to the second x-ray voltage, in order to measure the second projection dataset during the further orbit. In summary such a detector, the width of which covers the entire defined tissue area, can consequently record both projection datasets in only around one and a half rotations of the x-ray source. Thus both the high-energy image dataset and also the low-energy image dataset are measured almost simultaneously.

Especially preferably however the high-energy image dataset and the low-energy image dataset are recorded, (for instance the projection datasets needed for reconstruction of these image datasets), in a duel-source computed tomograph with two x-ray sources, wherein the x-ray sources simultaneously emit x-rays with different x-ray energy. I.e. the first of the x-ray sources emits x-rays of a first x-ray energy and simultaneously a second of the x-ray sources emits x-rays of a second x-ray energy differing from the first x-ray energy. Such dual-source computed tomographs have two emitter/detector systems, which are generally arranged rotatably offset by a 90° angle from each other together on the gantry around the tomograph longitudinal axis. The high-energy image dataset and the low-energy image dataset can thus be recorded simultaneously. As a result a high-energy image dataset and a low-energy image dataset are present in which differences resulting from movements of the object under examination are almost excluded, since the registration of the image datasets to one another is already provided by the measurement process itself and is perfect. In principle the use of more than two x-ray sources is also possible.

For identification of pixels which are to be assigned to necrotic tissue different criteria and parameters can be included.

In an especially simple and thus preferred variant a threshold analysis is performed in respect of the values of the pixels obtained for the area of the virtual contrast medium image to be segmented. In this case it is investigated for example whether the values, especially intensity values, of the pixels lie within the segmented area in the virtual contrast medium image above or below a specific threshold value. Depending on this it can then be determined whether this pixel is to be assigned to the vital tissue proportion or the necrotic tissue proportion.

In a first example embodiment there is provision for a threshold value to be predetermined beforehand for the threshold value analysis. A fixed threshold value can be involved here which is determined empirically beforehand and has been stored. Alternatively it is also possible for an operator to prespecify a threshold value, e.g. by manual input. For example a check can be made as to whether the intensity values of the pixels lie in the range of 0 to 10 HU, which indicates that these pixels are not to be assigned to tissue sections through which contrast medium has passed and thus belong to the necrotic tissue. On the other hand if the Hounsfield values lie in a range of 10 HU or above, this indicates that the pixels are to be assigned to the sections of tissue through which contrast medium has passed and therefore belong to the vital tissue in the defined tissue area.

In a second example embodiment of the threshold value analysis the threshold value is determined on the basis of the values of the pixels of the segmented area. This means that the measured values of the pixels are included for determining the threshold value. This has the advantage that offset-related displacement of the values of all pixels can be compensated for by an automatic appropriate selection of the threshold value. To this end for example the values of the pixels can be assigned to value intervals determined within the framework of the threshold analysis and a threshold value can be determined with reference to the interval boundaries of the two ranges of values.

In an especially preferred variant of at least one embodiment, a histogram is created for analysis based on the values of the pixels belonging to the segmented area of the virtual contrast medium image. In such a histogram the number of pixels can easily be plotted over the pixel value, e.g. the intensity value which has this excellent value. This histogram can be graphically displayed on a screen and can make it easier for an operator for example to determine a suitable threshold value.

As an alternative—even without a graphical presentation of the histogram—value intervals for necrotic tissue, vital tissue or especially preferably a simple threshold value to separate necrotic tissue and vital tissue can be automatically determined. This is generally possible through a simple search and analysis of the maxima and/or minima in the histogram. The automatically determined value intervals or the threshold value can also be initially displayed to an operator for confirmation or modification if necessary. In automatic histogram analysis it can especially also be established whether the data for defining a significant threshold value is at all suitable, i.e. whether a sensible determination of the proportion of necrotic tissue is possible at all with the available data. This is then only the case if a threshold value can be found which allows the values of the pixels to be assigned as uniquely as possible to the value interval of the necrotic tissue and to the value interval of the vital tissue.

A graphical presentation of the histogram allows the operator additional control in such cases.

The segmentation image dataset can—as mentioned above—be based solely on the high-energy on low-energy image dataset. Preferably however the segmentation image dataset involves what is referred to as a "mixed image dataset" which is determined by a weighted, pixel-by-pixel addition of values of the pixels from the high-energy image dataset and the low-energy image dataset. In this case the values of the pixels can be weighted with positive or negative weighting factors for the addition. If one of the two weighting factors is selected as negative, values of the pixels of the two image datasets are subtracted from one another.

In an example embodiment however, only positive weighting factors are used in order to achieve a true addition of the values of the pixels and thus to enhance the contrast in the segmentation image dataset which facilitates segmentation. In this case especially preferably weighting factors are selected which cause a weighting of the pixels of the high-energy and/or of the low-energy image dataset with a ratio of 7/10 to 3/10. If for example the high-energy image dataset is measured with an energy of 140 kV and the low-energy image dataset with an energy of 80 kV, an image impression is produced in the mixed image dataset through the weighting of 7/10 to 3/10 of a 120 kV measurement. This simplifies the segmentation of tumors in particular since the standard programs for oncological diagnosis of computed tomography image datasets are already oriented to the segmentation of tumors in image datasets which are measured with 120 kV. For the sake of completeness it should be mentioned that, as a variation from the said values, other values can also be used for measurement of the high-energy and the low-energy image dataset. Accordingly other weight ratios can be used.

Preferably the proportion of necrotic tissue of the defined tissue area is determined in relation to the overall defined tissue area. In this case the ratio of the volume of necrotic tissue to the overall volume of the defined tissue area is determined, e.g. as a percentage figure which specifies what percentage of the volume of the tumor still consists of vital tissue. If the constant volume proportion per pixel (which also means voxels of the same size) is used as the starting point, the number of pixels to be assigned by means of the histogram or the threshold value analysis to the necrotic tissue or vital tissue can be related to the overall number of pixels of the segmented volume.

In a further example embodiment, on the basis of the analysis an image dataset of at least one part of the defined tissue area is created in which such pixels which are assigned to necrotic tissue are shown in a different way to pixels of the defined tissue area which are assigned to vital tissue. This image dataset can then be output to an output device such as a screen or a printer and gives an operator an immediate overview about the location of necrotic and vital tissue in the defined tissue area. The information of such an image dataset reduces the risk of inadvertently removing necrotic tissue as part of the biopsy. In addition such a presentation, such as also the presentation of a histogram, allows a better assessment of the inhomogeneity of the defined tissue area, e.g. the tumor. It can thus be assessed whether the tumor merely has one contiguous area of vital tissue or many areas with vital tissue existing independently of one another.

The method allows a simple and reliable determination of the proportion of necrotic and vital tissue especially of a tumor and thus also a reliable assessment of the progress of therapy in the treatment of tumors. For this purpose especially preferably the inventive method can be repeatedly carried out at specific time intervals in order to document the increase in the necrotic tissue and the decrease in the proportion of vital tissue of the tumor tissue.

The x-ray system shown in FIG. 1 involves a dual-source-computed tomograph 1. This has a gantry accommodated in a gantry housing 6 able to be rotated around a system axis 9 (not explicitly shown) on which two emitter/detector systems 42, 44 are attached offset at an angle, which are each formed by an x-ray tube 2, 4 and a detector 3, 5 arranged opposite it on the gantry. An object under examination 12, here a patient, is located on a patient bed 8 able to be moved along a system axis 9 and can be pushed on this bed during the examination through a measurement field in the area of the emitter/detector systems 42, 44.

The dual-source computed tomograph 1 and if necessary also the image reconstruction can be controlled by an otherwise standard control device 7, which is configured specifically to carry out the inventive method for determining the proportion of necrotic tissue. The control device 7 for this purpose additionally has an inventively constructed image processing device 10. The image reconstruction device 10 can feature one or more interacting memories and processors, in order to implement a computer program product for carrying out the method for determining the proportion of necrotic tissue. This means that the components of the image processing device 10 explained below can at least partly be realized in the form of software modules. In this case memories and processors can also be used which are otherwise used by the control device 7 for other tasks, e.g. the control of the tomograph.

The image processing device 10 has an image data interface 24, with which a high-energy image dataset and a low-energy image dataset can be read in. The image processing device 10 also has a contrast medium image detection unit 26 which, on the basis of the high-energy image dataset and of the low-energy image dataset, determines a virtual contrast medium image (also referred to below as a virtual "iodine" image). The image processing device 10 further comprises a segmentation unit 28, with which a segmentation of the defined tissue area can be created in a segmentation image dataset based on the high-energy image dataset and the low-energy image. Furthermore the image processing device 10—as a variant of a segmentation image dataset creation unit—has an addition unit 64 for the pixel-by-pixel addition of values of the high-energy image dataset and the low-energy image dataset. As a further unit the image processing device 10 has a referencing unit 30, with which a segmentation result can be transferred into the contrast medium image for segmenting the tissue area in the virtual contrast medium image 20. Finally the image processing device 10 has an analysis unit 32, with which an analysis of values of the area to be segmented of the pixels belonging to the virtual contrast medium image can be carried out for identification of pixels which are to be assigned to necrotic tissue.

In the measurement of the high-energy image dataset and the low-energy image dataset the x-ray tubes 2, 4 of the emitter/detector systems 42, 44 are operated with different x-ray energies, i.e. different x-ray voltages. For example the x-ray tubes 2 of the first system 42 are operated at 140 kV and the x-ray tubes 4 of the second system 44 at 80 kV.

The orbit of the two emitter/detector systems 42, 44 around the object under examination 12 creates projection datasets in the form of sinograms. Through a normal—and therefore not explained in any greater detail here—filtered back projection and/or reconstruction, a high-energy image dataset and a low-energy image dataset respectively from inside the object under examination 12 can be created from such projection datasets or sinograms after an injection of contrast medium at the object under examination.

The high-energy image dataset and the low-energy image dataset are as a rule three-dimensional volume data, wherein such data can also be formed, depending on the recording and reconstruction technique, by a stack of two-dimensional slice images.

An example embodiment of the inventive method is now explained in more detail, making additional reference to FIGS. 2 to 5.

Figure 3:
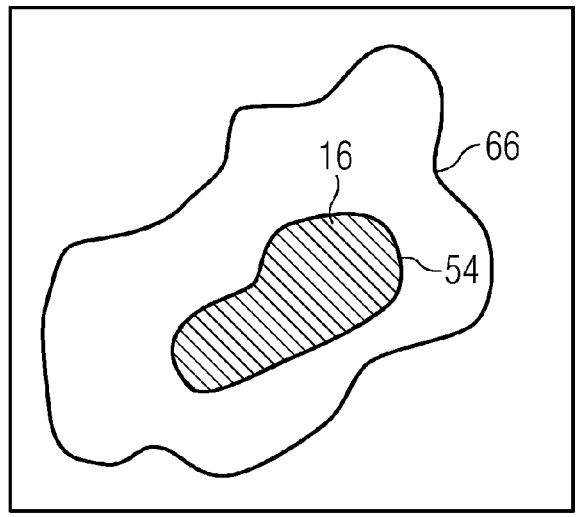
FIG. 3 shows a schematic diagram of a tissue area to be examined.

An organ 66 with a selected defined tissue area 16 is to be examined, in which in the present exemplary embodiment a tumor 16 is involved, which is delimited by a tumor boundary 54 (see FIG. 3). The tumor 16 here has a proportion of necrotic tissue 14, which is surrounded by an outer edge of vital tissue 18 (shown in FIG. 4).

Before the beginning of the actual examination a contrast medium KM is injected (see FIG. 2), usually a medium containing iodine, into the object under examination 12 (see FIG. 1). After the contrast medium KM has been applied the contrast medium collects in vital tissue 18 of the tumor 16. The necrotic tissue 14 on the other hand does not have blood running through it like the vital tissue 18, so that no contrast medium or in any event only very little contrast medium accumulates in the area of the necrotic tissue 14.

In a first step (see FIG. 2) a dual-energy measurement DE is then carried out comprising a first recording AUH with high x-ray energy and a second recording AUN with low x-ray energy. For the recording AUH for example the first x-ray tube 2 has an x-ray voltage of 140 kV applied to it, for the second recording AUN the second x-ray tube 4 has an x-ray voltage of 80 kV applied to it.

During the dual-energy measurement DE the projection datasets described above which are transferred to the image processing device 10 (the FIG. 1) are measured. These projection datasets 56 are subjected to a reconstruction RE, so that as a result of the reconstruction RE a high-energy image dataset 46 and a low-energy image dataset 48 are present.

The high-energy image dataset 46 and the low-energy image dataset 48 are subjected in a further step to a weighted addition AD, in order to create a mixed image dataset 22 as a segmentation image dataset 22. This is done in an addition unit 64 of the image processing device 10. In this case a factor of 7/10 is used as weighting factor for the image values of the high-energy image dataset 46 and a factor of 3/10 is used for the image values of the low-energy image dataset 48. The intensity values thus created of the pixels of the segmentation image dataset 22 thus correspond to image values which would be obtained with a measurement of an energy image dataset of 120 kV.

In a further step a segmentation SE of the tumor 16 in the mixed image dataset 22 is carried out. This can be carried out manually by an operator or image processing programs suitable for this purpose are used. Since the mixed image dataset 22 corresponds to a 120 kV image dataset, a program normal in oncology for segmentation of tumors can be used, which operates for example with a marking-based segmentation. To do this the operator can for example draw a "/" with a mouse pointer (any given diagonal over the tumor) in the image data shown on a screen of a graphical user interface. On the basis of the Hounsfield values of the pixels marked by the stroke automatic parameters are then determined, with the aid of which the automatic segmentation is undertaken. The segmentation unit 28 of the image processing device 10 can accordingly be realized as a program module with access to a suitable user interface.

Figure 4:
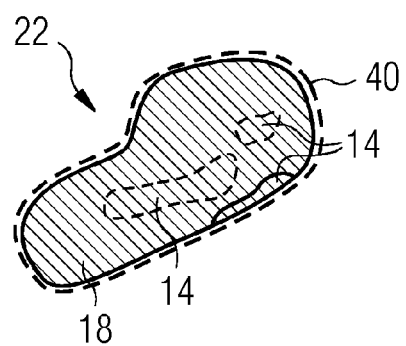
FIG. 4 shows a schematic diagram of a selected tissue area after a segmentation.

The segmentation result 40 of the segmentation SE describes the boundaries of the tumor 16 or contains the location information about all voxels belonging to the tumor 16 within the boundaries of the tumor 16 identified in the segmentation. In FIG. 4 an image of the tumor 16 segmented from the mixed image dataset is presented. In this mixed image the necrotic tissue 14 is not able to be distinguished from the vital tissue 18 in an optimum manner.

In a further step ER a virtual contrast medium image 20 is generated as a virtual iodine image 20 from the high-energy image dataset 46 and the low-energy image dataset 48 in the known manner. This is done in the contrast medium determination unit 26 of the image processing device 10 (see FIG. 1). In this iodine image 20 the pure iodine intensity values are shown at the individual pixels, i.e. tissue through which blood does not run has a Hounsfield value of approx. 0 HU in this iodine image.

Figure 5:
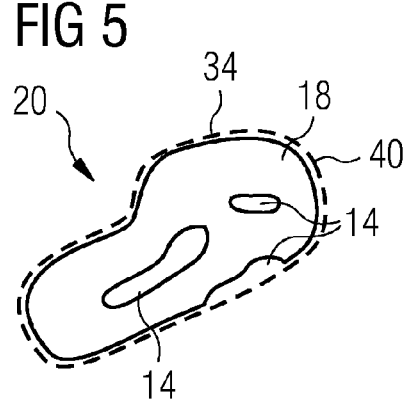
FIG. 5 shows a schematic diagram of a virtual contrast medium image.

The segmentation result 40 from FIG. 4 is then transferred in a further step UE into the virtual contrast medium image 20. This is performed by the referencing unit 30 of the image processing device 10. As a result of this step UE a segmented area 34 is now present in the virtual iodine image 20, which encloses the proportion of necrotic tissue 14 and the proportion of vital tissue 18. An image of the segmented tumor in the iodine image 20 is shown in FIG. 5. Since the contrast medium containing iodine has accumulated in vital tissue 18, the pixels in this area exhibit higher values, i.e. intensity or Hounsfield values, than in the necrotic tissue 14 in which the Hounsfield values are close to 0 HU.

An analysis unit 32 of the image processing device 10 now analyses the values of pixels which belong to the segmented area 34 of the virtual iodine image 20 in order to identify pixels which are to be assigned to necrotic tissue 14.

Figure 6:
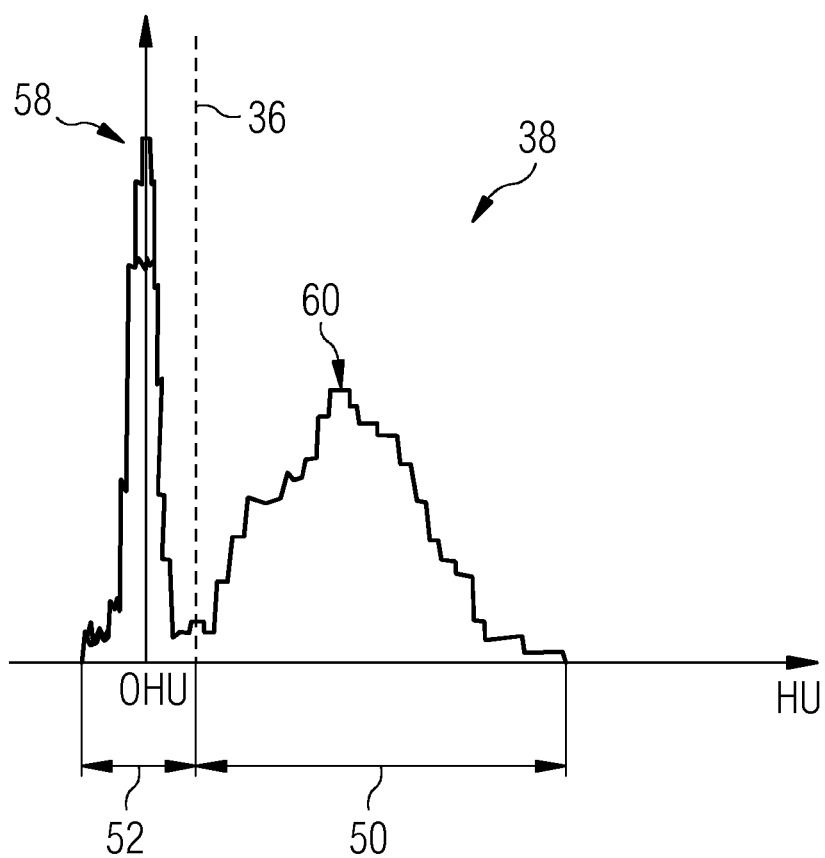
FIG. 6 shows an example of a histogram for use in an inventive method and FIG. 7 shows an example of an image dataset.

For evaluation, in an "analyse" AN step a histogram 38 is created by the analysis unit 32, as is shown in FIG. 6 for example. The histogram 38 specifies the distribution of different intensity values in accordance with their frequency. To this end all pixels with an identical Hounsfield value, or with a Hounsfield value within a specific value range, are simply summed. It is immediately evident that the histogram 38 has two large value intervals 50, 52. Since contrast medium hardly accumulates or does not accumulate at all in necrotic tissue 14, the pixels of the necrotic tissue 14 are distributed around 0 HU. Pixels of the non-necrotic, vital tissue proportion 18 exhibit intensity values above 10 Hu.

Thus the value distribution of the histogram 38 shows two maxima 58, 60, which lie approximately in the center of the respective value intervals 50, 52. On the basis of this histogram 38 and the distribution of values in the two value ranges 50, 52 the analysis unit 32 can determine a value for a threshold value in a step of a threshold value analysis SW. This involves the HU value at which the minimum between the two maxima 58, 60 is located. All these values can be found very simply automatically in the histogram with conventional algorithms. The threshold value 36 then allows the pixels to be assigned to the proportion of necrotic tissue 14 and the proportion of vital tissue 18.

Figure 2:
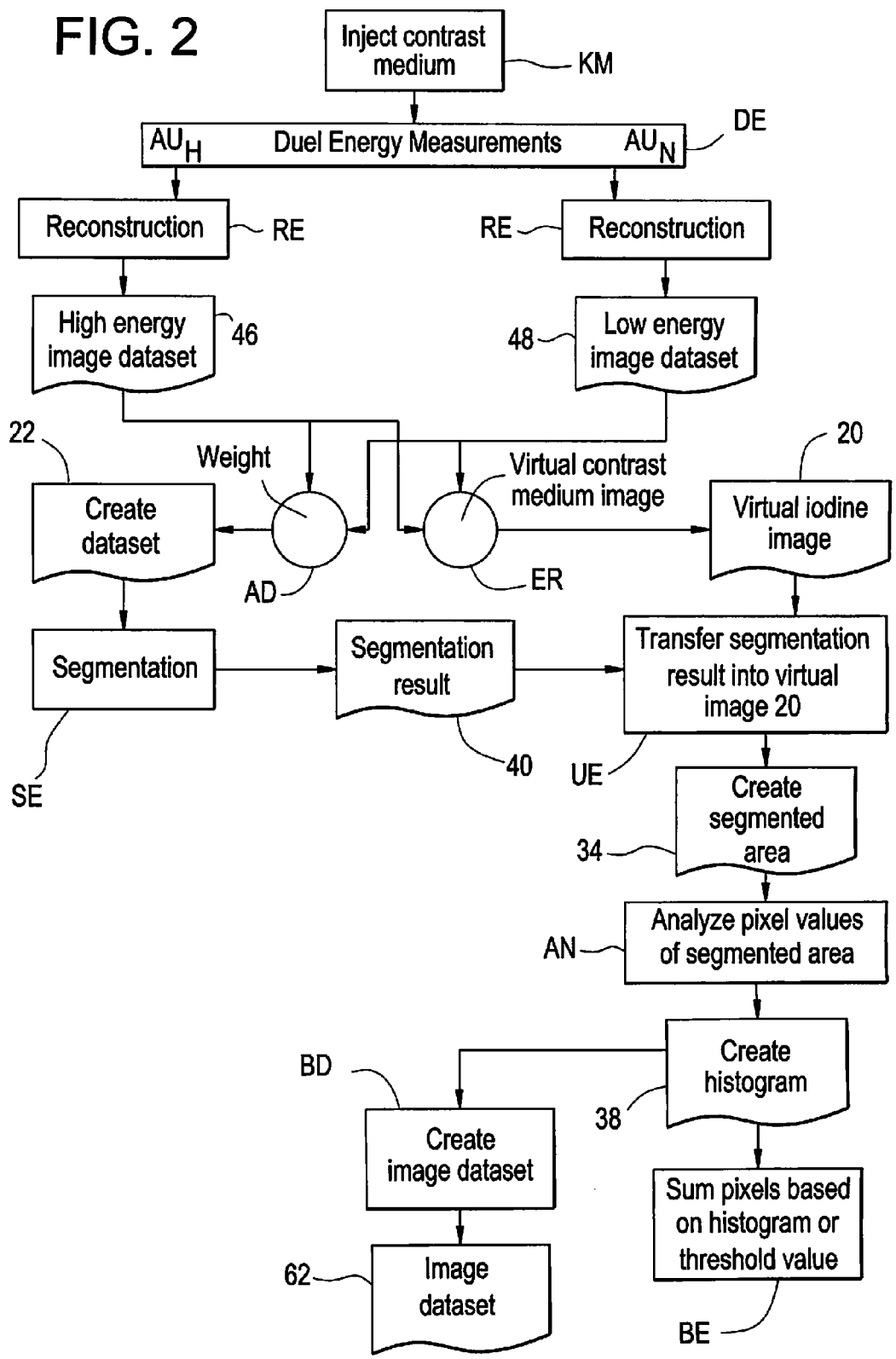
FIG. 2 shows a flowchart of a possible example embodiment of the inventive method.

Thus a simple determination of the proportion of necrotic tissue 14 in the tumor 16 by the analysis unit 32 is also possible, which is done in FIG. 2 in a step BE. To this end the number of pixels, i.e. voxels or pixels, of the respective value intervals 50, 52 is simply counted by the analysis unit 32. In this case the sum of all pixels in the two value intervals 50, 52 corresponds to the total volume of the tumor 16, while the number of voxels in the necrotic value range 52 corresponds to the volume of the necrotic tissue proportion 14. If the two count values are now related to one another, the result is a specification in percent of the proportion of necrotic tissue 14 of the tumor 16.

As an alternative, in step BE the proportion of necrotic tissue 14 of the tumor 16 can also be determined by the analysis unit 32 without using a histogram 32 but using a threshold value which is determined empirically and has then been pre-specified at a fixed level. The total number of voxels of the tumor 16 and the number of voxels of which the values, i.e. intensity values lie above the threshold value 36 and thus belong to the vital tissue 18 are determined and expressed as a ratio to one another.

Optionally in a step "image dataset creation" BD the analysis unit 32 can create an image dataset 62 in which the areas with necrotic tissue 14 are shown optically in a different way from the areas with vital tissue 18.

This also requires the information to define which pixels belong to necrotic tissue and which to vital tissue 18. In principle it is possible for the analysis unit 32 to refer back again in step BD to the threshold value 36, which was already used in step BE. The threshold value 36, as already described, can have been obtained using a histogram 38, or an empirically defined and then fixed prespecified threshold value 36 is used. The pixels can then be identified by color in an image view for example, depending on whether their value lies above or below the threshold value.

Figure 7:
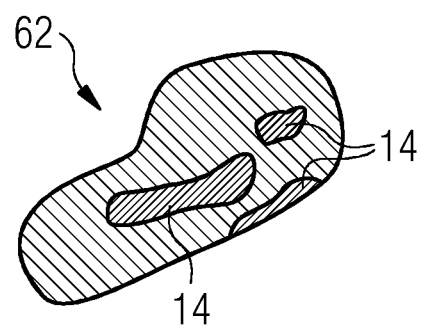

Accordingly for a graphic presentation, the voxels or pixels of the image dataset 62 which belong to the respective value intervals 50, 52 can then be identified graphically by different coloring or by assignment of different gray values. An example of such a part of a marked image dataset only showing the segmented tumor is illustrated schematically in FIG. 7, with here necrotic tissue 14 and vital tissue 18 simply being represented by different crosshatching.

This type of marked presentation can then preferably be carried out again in the complete mixed image dataset or in another complete image so that the observer is shown the spatial arrangement and extent of the necropsy areas 14 and the vital tissue 18 of the tumor within the overall anatomy. This makes it easier for example to ensure that only vital tissue 18 is removed in a biopsy.

Finally it is pointed out once again that the methods and devices described above merely involve preferred exemplary embodiments of the invention and that the invention can be varied by the person skilled in the art without departing from the area of the invention, in as far as it is predetermined by the claims. For example in the method sequences described above, method steps which are specified executing in parallel can if necessary also be executed in another sequence one after the other. For reasons of completeness it is also pointed out here that the use of the indefinite article "a" or "an" does not exclude the features concerned also being able to be present multiple times.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for determining a proportion of necrotic tissue in a defined tissue area of an object under examination based on a relatively high-energy image dataset including the tissue area of the object under examination and a relatively low-energy image dataset including the tissue area of the object under examination, the method comprising:
determining a virtual contrast medium image based on the relatively high-energy image dataset and the relatively low-energy image dataset;
segmenting the tissue area into a segmentation image dataset based on at least one of the relatively high-energy image dataset and the relatively low-energy image dataset, and producing a segmentation result;
transmitting the segmentation result into the virtual contrast medium image and segmenting the tissue area in the virtual contrast medium image based upon the segmentation result; and
executing an analysis of values of pixels belonging to the segmented tissue area of the virtual contrast medium image to determine the proportion of necrotic tissue in the defined tissue area by identifying pixels assignable to the necrotic tissue.

2. The method as claimed in claim 1, wherein, within the method, images of the relatively high-energy image dataset comprising the tissue area of the object under examination and of the relatively low-energy image dataset comprising the tissue area of the object under examination are recorded by way of x-ray measurement with relatively different x-ray energies after application of a contrast medium to the object under examination.

3. The method as claimed in claim 2, wherein the images of the relatively high-energy image dataset and of the relatively low-energy image dataset are recorded in a dual-source computed tomograph with two x-ray sources, whereby the two x-ray sources simultaneously emit x-rays with different energies.

4. The method as claimed in claim 1, wherein, for identification of pixels assignable to the necrotic tissue, a threshold value analysis is performed in respect of the values of pixels belonging to the segmented area of the virtual contrast medium image.

5. The method as claimed in claim 4, wherein a threshold value is specified for threshold value analysis.

6. The method as claimed in claim 4, wherein a threshold value for the threshold value analysis is determined on the basis of the values of the pixels of the segmented area.

7. The method as claimed in claim 6, wherein a histogram is created for analysis on the basis of the values of the pixels belonging to the segmented area of the virtual contrast medium image.

8. The method as claimed in claim 7, wherein the threshold value is determined on the basis of the histogram.

9. The method as claimed in claim 1, wherein the segmentation image dataset is a mixed image dataset, determined by a weighted, pixel-by-pixel addition of values of the pixels from the relatively high-energy image dataset and the relatively low-energy image dataset.

10. The method as claimed in claim 1, wherein a proportion of necrotic tissue of the defined tissue area is determined in relation to the entire defined tissue area.

11. The method as claimed in claim 10, wherein, based upon the analysis, an image dataset of a least a part of the defined tissue area is created, in which pixels which are assigned to necrotic tissue are shown differently from pixels of the defined tissue area which are assigned to a vital tissue.

12. The method as claimed in claim 10, wherein the defined tissue area comprises tumor tissue.

13. The method as claimed in claim 1, wherein, based upon the analysis, an image dataset of a least a part of the defined tissue area is created, in which pixels which are assigned to necrotic tissue are shown differently from pixels of the defined tissue area which are assigned to a vital tissue.

14. The method as claimed in claim 1, wherein the defined tissue area comprises tumor tissue.

15. The method as claimed in claim 1, wherein a histogram is created for analysis on the basis of the values of the pixels belonging to the segmented tissue area in the virtual contrast medium image.

16. The method as claimed in claim 15, wherein a threshold value is determined on the basis of the histogram.

17. An image processing device to determine a necrotic proportion in a defined tissue area of an object under examination, the image processing device comprising:
an image dataset interface, configured to read in a relatively high-energy image dataset including the tissue area of the object under examination and a relatively low-energy image dataset including the tissue area of the object under examination, each of the relatively high and low-energy image datasets being generated from x-ray measurements with relatively different x-ray energies after application of a contrast medium to the object under examination;

a contrast medium image determination unit, configured to determine a virtual contrast medium image based on the relatively high-energy image dataset and the relatively low-energy image dataset;

a segmentation unit, configured to segment the tissue area in a segmentation image dataset, created based upon at least one of the relatively high-energy image dataset and the relatively low-energy image dataset, and produce a segmentation result;

a referencing unit, configured to transfer the segmentation result into the virtual contrast medium image for segmenting the tissue area in the virtual contrast medium image; and an analysis unit, configured to carry out an analysis of values of pixels belonging to the area to be segmented of the virtual contrast medium image in order to determine a necrotic proportion in a defined tissue area of an object under examination by identifying pixels to be assigned to necrotic tissue.

18. A computed tomography system, comprising an image processing device as claimed in claim 17.

19. A dual-source-computed tomography system, comprising an image processing device as claimed in claim 17.

20. A memory of an image processing device including program code sections, stored therein, to execute the method as claimed in claim 1 when the program code sections are executed in the image processing device.

21. An image processing device comprising the memory of claim 20.

22. A non-transitory computer readable medium including program segments for, when executed on a computer device, causing the computer device to implement the method of claim 1.

* * * * *